United States Patent [19]

Fukuda

[11] 4,224,947
[45] Sep. 30, 1980

[54] SUTURING APPARATUS

[76] Inventor: Mamoru Fukuda, 1260 Hardy Dr., Bridge City, Tex. 77611

[21] Appl. No.: 9,476

[22] Filed: Feb. 5, 1979

[51] Int. Cl.³ .............................................. A61B 17/06
[52] U.S. Cl. ................................................ 128/340
[58] Field of Search ........................ 128/339, 340, 329

[56] References Cited

U.S. PATENT DOCUMENTS

| 919,138 | 4/1909 | Drake et al. | 128/340 |
|---|---|---|---|
| 2,365,647 | 12/1944 | Ogburn | 128/340 |
| 2,611,366 | 9/1952 | Mull | 128/340 |
| 3,013,559 | 12/1961 | Thomas | 128/340 |
| 3,840,017 | 10/1974 | Violante | 128/340 |

FOREIGN PATENT DOCUMENTS 259450 4/1912 Fed. Rep. of Germany ........... 128/340

Primary Examiner—Dalton L. Truluck
Attorney, Agent, or Firm—Gunn, Lee & Jackson

[57] ABSTRACT

An improved suturing apparatus for non-continuous suturing of ruptured or incised skin. Suturing thread is held in an enclosed reel and fed through tubing into a hollow suturing needle. The suturing thread exits the hollow suturing needle through an aperture proximate to the tip of the hollow suturing needle. Needle-holding forceps hold the hollow suturing needle and assist in forcing the needle tip through the tissue to be sewn. Regulable feed means for moving the thread, such as compressed gas, is introduced into the enclosed reel, tubing or hollow suturing needle. The compressed gas moves toward the lower pressure area created by the aperture in the hollow suturing needle, also pushing and carrying the suturing thread out the aperture. The needle tip is pulled back out of the tissue, leaving the extended thread in the tissue. A sharp edge on the needle aperture is used to cut the suturing thread.

9 Claims, 7 Drawing Figures

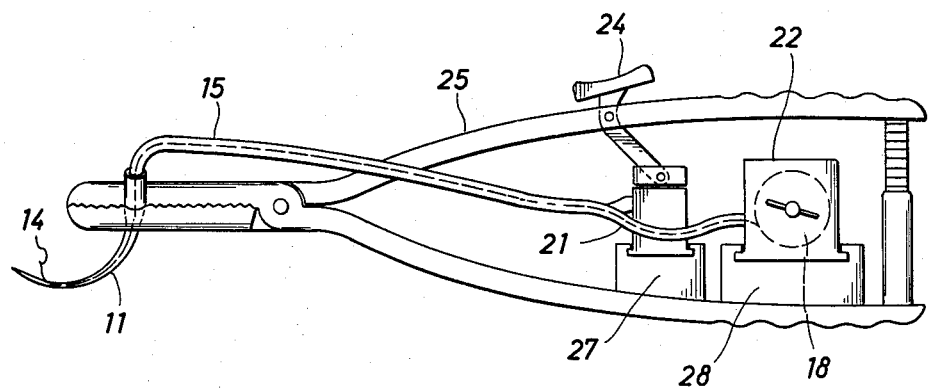
FIG. 4
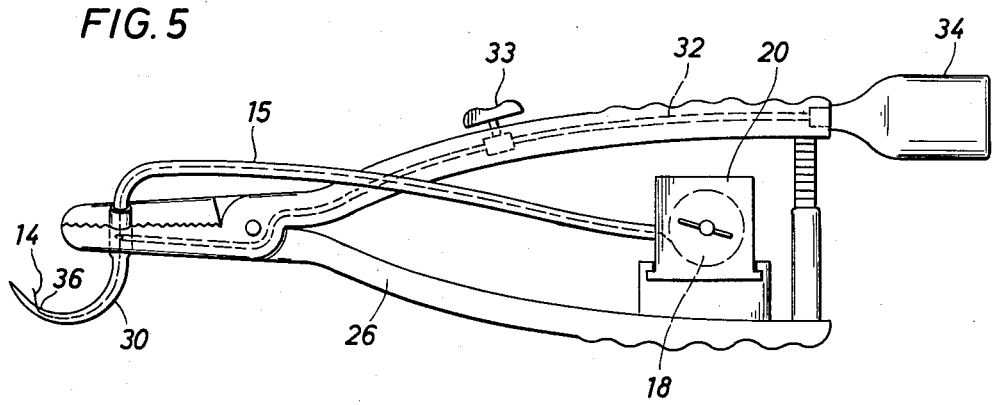
FIG. 5
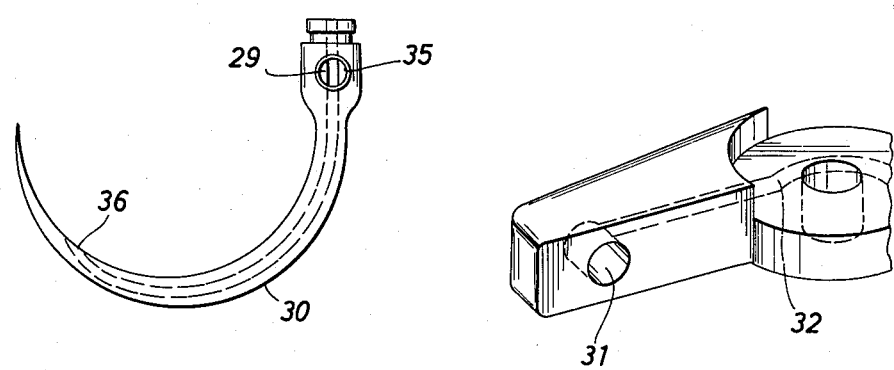
FIG. 7
FIG. 6

SUTURING APPARATUS

BACKGROUND OF THE INVENTION

1. Field of the Invention

This invention relates to an improved apparatus for suturing the lips or edges of ruptured or incised skin.

2. Description of the Prior Art

The present method of suturing ruptured or incised skin uses a needle with suturing thread attached to the blunt end thereof, needle-holding forceps, and scissors or other cutting device. In a typical suturing operation, there are ten separate actions normally employed for completion of each suture. These are:

1. The thread is attached to the suturing needle.
2. Needle-holding forceps are cramped onto the needle.
3. The pointed end of the needle is then inserted through the tissue to be sutured until the tip of the needle penetrates the tissue on the other side.
4. The needle-holding forceps are uncramped from the needle.
5. The tip of the needle that has been forced through the tissue is cramped by the needle-holding forceps.
6. The needle-holding forceps are used to pull the needle with attached thread through the tissue.
7. The forceps are uncramped.
8. The thread is cut at the end closest to its source, such as a spool, with a cutting device, usually a pair of scissors. (This step may be accomplished first by cutting thread in a predetermined length.)
9. The thread is removed from the blunt end of the needle.
10. The ends of the thread are then secured by tying to prevent the thread from "pulling out" of the sutured tissues.

This procedure is time consuming and an inefficient use of the user's motions.

Therefore, a feature of this invention is to provide an improved suturing apparatus that eliminates removing and reattaching the needle-holding forceps to the needle after each suture.

Another feature of this invention is to provide an improved suturing apparatus that eliminates rethreading the needle prior to each suture.

Yet another feature of this invention is to provide an improved suturing apparatus including a cutting device, thereby eliminating a separate cutting device, such as a pair of scissors.

SUMMARY OF THE INVENTION

The invention embodiments disclosed herein include a hollow suturing needle having an aperture near its pointed end wide enough to accommodate the passage of suturing thread. The aperture preferably has at least one sharpened edge or area. Suturing thread passes from an enclosed holding chamber including a relatively friction-free means, such as a reel, for easily unraveling the thread into tubing attached to the holder and the suturing needle. Feed means, such as compressed gas, is introduced into the tubing, holding chamber, or hollow suturing needle for actuating the reel and for advancing the suturing thread through the hollow suturing needle. The compressed gas is preferably emitted from a compression chamber either apart from or incorporated into the enclosed holding chamber, and includes a valve to regulate the flow of the gas, thereby exerting an advancing pressure on the suturing thread. A winding handle is preferably located outside the enclosed suturing thread holding chamber and attached to the reel enabling the user to rewind excess thread by hand.

BRIEF DESCRIPTION OF THE DRAWINGS

So that the manner in which the above-recited features, advantages and objects of the invention, as well as others which will become apparent, are attained and can be understood in detail, more particular description of the invention briefly summarized above may be had by reference to the embodiments thereof which are illustrated in the appended drawings, which drawings form a part of this specification. It is to be noted, however, that the appended drawings illustrate only typical embodiments of the invention and are therefore not to be considered limiting of its scope, for the invention may admit to other equally effective embodiments.

In the drawings:

FIG. 4 is a pictorial illustration of a preferred embodiment of the invention showing one means for retaining the compression chamber and suturing thread reel.

FIG. 5 is a pictorial illustration of an alternate preferred embodiment of the invention showing another means for advancing thread through the suturing needle.

FIG. 6 is a pictorial illustration showing an enlarged view of the suturing needle used in conjunction with FIG. 5.

FIG. 7 is a pictorial illustration showing an enlarged view of the needle-holding forceps used in conjunction with FIG. 5.

DESCRIPTION OF THE PREFERRED EMBODIMENTS

Figure 1:
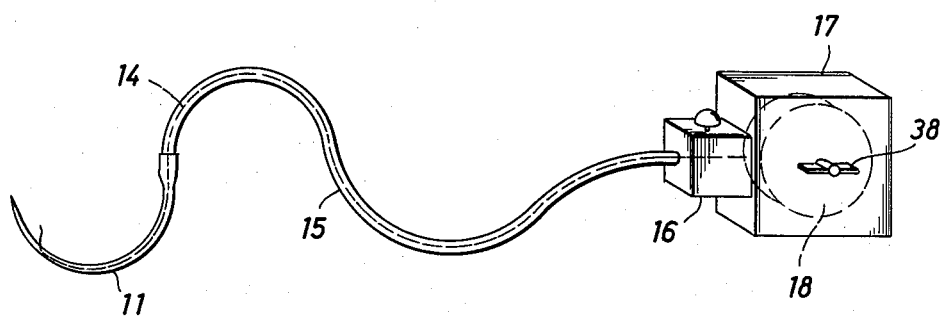
FIG. 1 is a pictorial illustration of a preferred embodiment of the invention disclosed herein.

Now referring to the drawings, and first to FIG. 1, an improved suturing apparatus in accordance with the present invention is shown. Hollow suturing needle 11 is connected to one end of tubing 15. The other end of tubing 15 is attached to compression chamber 17, thereby creating an enclosed passage from compression chamber 17 to hollow suturing needle 11. A continuous strand of suturing thread 14 is preferably wrapped around and held by reel 18 rotatably attached either directly to the walls of the compression chamber 17 or to a base (not shown) attached to the compression chamber. Further, suturing thread 14 is run through tubing 15, into hollow suturing needle 11, and out an aperture in the tip of the hollow suturing needle. Valve 16, located proximate to the intersection of tubing 15 with compression chamber 17, regulates release of compressed gas into tubing 15. Tubing 15 is preferably made of flexible plastic or metal to facilitate easy exchange and adjustment of hollow suturing needle 11. If it is desirable to locate release valve 16 away from compression chamber 17, tubing 15 should be sufficiently strong to withstand the pressure of the compressed gas to be contained therein. A handle 38 for rewinding excess thread ejected or fed out of suturing needle 13 is externally located on compression chamber 17.

Figure 2:
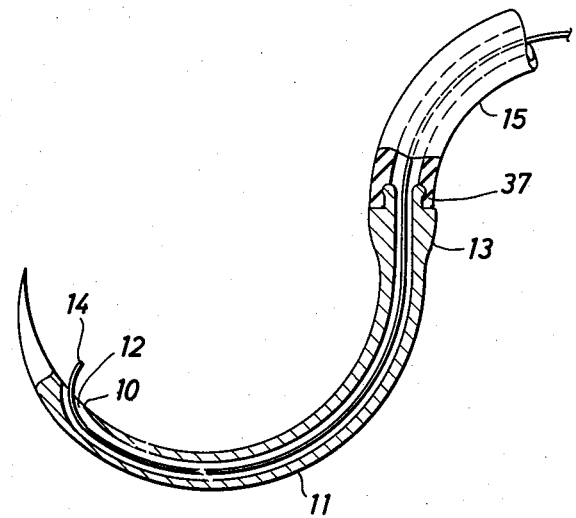
FIG. 2 is an enlarged view of the needle attached to the tubing taken along line 2—2 in FIG. 1.

FIG. 2 is an enlarged view of hollow suturing needle 11 attached to tubing 15 illustrated in FIG. 1. Gas released from compression chamber 17 illustrated in FIG. 1 moves through tubing 15 and hollow suturing needle 11 toward the lower pressure area of aperture 12 located proximate to the tip of hollow suturing needle 11. The expanding gas also pushes and carries suturing thread 14 along the same path toward and out aperture 12 in hollow suturing needle 11.

FIG. 2 also illustrates hollow suturing needle 11 as preferably being thicker at the blunt end 13. The thicker blunt end 13 facilitates connection with tubing 15 and provides greater strength, resisting fracture when cramped by needle-holding forceps during the suturing process. One method of connecting tubing 15 with suturing needle 13 utilizes an outwardly turned lip 37 on the blunt end of such suturing needle, the external dimension of the lip being somewhat larger than the internal channel of tubing 15 to provide a snug press fit. Suturing needle 13 mates with tubing 15 when lips 37 are pushed into the channel in tubing 15. However, any conventional mating means capable of withstanding the pressure generated when compressed gas is the feed means may be used.

Sharp edge 10 is preferably located on the back lips of aperture 12. After the needle has passed through the tissues to be sutured, sufficient compressed gas is released forcing the desired amount of suturing thread 14 through aperture 12. The needle is removed leaving the suturing thread 14 in the suture. A sharp backward pull on the suturing thread near sharp edge 10 cuts such thread in preparation for knotting.

Figure 3:
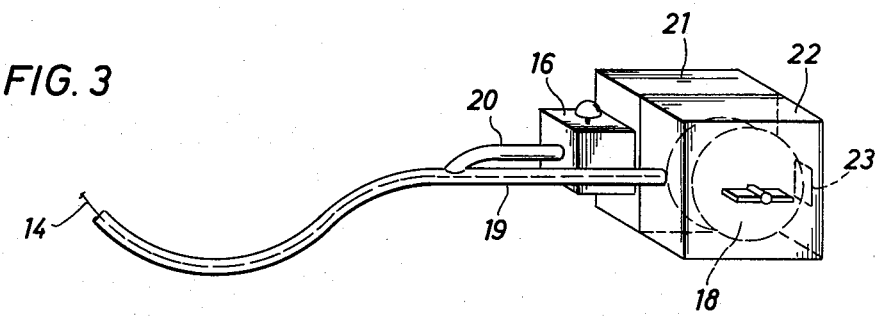
FIG. 3 is a pictorial illustration of an alternate preferred embodiment of the invention disclosed herein.

FIG. 3 illustrates an alternate preferred embodiment of this invention. In this embodiment, suturing thread reel 18 is held in a suturing thread holding chamber 22 separate from compression chamber 21. Tubing 15 divides into two separate tubes proximate to the two chambers. First division tube 19 carries the suturing thread 14 and connects to suturing thread holding chamber 22. Second division tube 20 connects to compression chamber 21. Valve 16 located on or proximate to compression chamber 21 is capable of releasing gas from such compression chamber. Suturing thread holding chamber 22 preferably has a one-way trap door 23 permitting air to enter when necessary to avoid a vacuum phenomenon.

FIG. 4 illustrates a preferred embodiment of this invention showing compression chamber 21 and suturing thread holding chamber 22 retained by needle-holding forceps 25.

Needle-holding forceps 25 preferably cramp hollow suturing needle 11 during the suturing process, increasing the leverage and pressure that can be applied in forcing the needle through the lips of the incised or ruptured skin. Compression chamber 21 and suturing thread holding chamber 22 are preferably sufficiently flat with regard to the plane of needle-holding forceps 25, to prevent or reduce interference with the user's grip on such needle-holding forceps. The two chambers can be secured to needle-holding forceps 25 inside the two gripping arms by any conventional method using, for example, tension spring wires, tension coils, or straps. Alternatively, a base may be constructed on needle-holding forceps 25 to hold and facilitate replacement of the chambers, such as compression chamber base 27 and suturing thread holding chamber base 28.

FIG. 5 illustrates an alternate preferred embodiment of this invention. One gripping arm of needle-holding forceps 26 has a channel 32 running from the non-cramping end to the point on the cramping end where the suturing needle is cramped. A compressed gas cartridge, such as preferably nitrogen, which is non-toxic and has little effect on the temperature of the apparatus, is attachable to channel 32 on the grip end of needle-holding forceps 26. Compressed gas cartridge 34 is preferably lightweight and sufficiently small in size so as not to impede the movements of the user. Valve 33 regulates the release of compressed gas from compressed gas cartridge 34, after such cartridge is attached. The location of valve 33 does not affect its function, although for convenience to the user to provide easy access, such valve is located on the outside portion of the gripping arm of needle-holding forceps 26.

Suturing thread 14 is wrapped around a low friction, rotatable reel 18 encased in suturing thread holder 22. Suturing thread holder 22 is preferably attached to needle-holding forceps 26. Tubing 15 is attached at one end to hollow suturing needle 30 and at the other end to suturing thread holder 22. Suturing thread 14 passes from reel 18 through tubing 15 into hollow suturing needle 30 and out aperture 36 proximate to the tip of suturing needle 30. When released by valve 24, compressed gas travels through channel 32 into hollow suturing needle 30 (see FIG. 7), pushing and carrying suturing thread 14 as the compressed gas exits the apparatus through aperture 36. Suturing thread holding chamber 22 again preferably has a one-way trap door 23 permitting air to enter when necessary to avoid a vacuum phenomenon.

FIG. 6 shows an enlarged view of the channel containing cramping arm of needle holding forceps 26. Compressed gas travels through channel 32 toward the low pressure area created by aperture 31.

FIG. 7 shows an enlarged view of hollow suturing needle 30 having an aperture 20 corresponding in size to such aperture illustrated in FIG. 6. A washer, rim, or combination thereof, 35 preferably is used to mate hollow suturing needle 30 with aperture 31 in needle-holding forceps 26, preventing leakage of the compressed gas.

Again, a sharp edge 37 is preferably placed on the back lip of aperture 36, enabling the user to cut the thread by pulling suturing thread 14 back against such sharp edge.

While particular embodiments of the invention have been shown and described, it will be understood that the invention is not limited thereto, since many modifications may be made and will become apparent to those skilled in the art. For example, the compression chamber in any of the embodiments could be located on the floor and a foot pedal could be used as the release mechanism permitting compressed gas to escape from such chamber into tubing eventually attached to the hollow suturing needle.

What is claimed is:

1. A suturing tool comprising:
   (a) a hollow needle having a sharp tip and a blunt end, said needle including an exit aperture proximate said tip;
   (b) reel means for holding a quantity of thread for feeding through said hollow needle;
   (c) feed means for actuating said reel means for advancing thread through said needle;

(d) flexible passage means connecting said needle to said reel means providing a passage for advancing the thread through said needle;

(e) handle means for rewinding excess thread advanced by said reel means; and (f) forceps means for manipulating said needle for suturing ruptured or incised tissue.

2. A suturing tool in accordance with claim 1, wherein one side of said exit aperture is sharpened for cutting off the thread exiting therefrom with the application of side pressure on said needle.

3. A suturing tool in accordance with claim 1, wherein said feed means includes a compression chamber encasing said reel means and a valve, the opening of said valve causing compressed gas within said chamber to exert an advancing pressure on said thread.

4. A suturing tool in accordance with claim 3, wherein said compressed gas is nitrogen or other gasses.

5. A suturing tool in accordance with claim 3 wherein said forceps means includes two gripping arms pivotally connected adjacent one end and spaced by spring means at the other end and wherein said feed means and said reel means are secured to said gripping arms.

6. A suturing tool in accordance with claim 5 wherein said forceps means includes a channel extending through one of said gripping arms in fluid communication with said needle and said feed means, said channel terminating in an aperture in said one gripping arm mating with a needle aperture provided in the blunt end of said needle.

7. A suturing tool in accordance with claim 6 wherein said one gripping arm includes valve means for regulating the release of said compressed gas from said compression chamber.

8. A suturing tool in accordance with claim 7 wherein said compression chamber is a gas cartridge connected to said one gripping arm.

9. A suturing tool in accordance with claim 1, wherein said feed means includes a compression chamber apart from said reel means, said chamber having a release valve, thread leaving said reel means passing through a common conduit connected to the downstream side of said valve, the opening of said valve causing compressed gas within said chamber to exert an advancing pressure on said thread.

* * * * *